United States Patent
Frigg et al.

(10) Patent No.: US 8,043,333 B2
(45) Date of Patent: Oct. 25, 2011

(54) DYNAMIC STABILIZATION SYSTEM

(75) Inventors: Robert Frigg, Bettlach (CH);
Christopher Stabley, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 738 days.

(21) Appl. No.: 12/133,832

(22) Filed: Jun. 5, 2008

(65) Prior Publication Data

US 2008/0306536 A1   Dec. 11, 2008

Related U.S. Application Data (60) Provisional application No. 60/942,821, filed on Jun. 8, 2007.

(51) Int. Cl.
*A61B 17/70* (2006.01)
*A61B 17/04* (2006.01)

(52) U.S. Cl. .......................... 606/246; 606/280; 606/286

(58) Field of Classification Search .................. 606/278, 606/279, 100, 318, 71, 246, 301, 280, 286, 606/264, 254, 319, 305
See application file for complete search history.

(56) References Cited

U.S. PATENT DOCUMENTS

| | | | |
|---|---|---|---|
| 4,959,064 A | 9/1990 | Engelhardt | 606/65 |
| 5,074,865 A | 12/1991 | Fahmy | 606/54 |
| 5,318,282 A | 6/1994 | Schaefer | 267/136 |
| 5,480,401 A | 1/1996 | Navas | 606/61 |
| 5,743,912 A | 4/1998 | Lahille et al. | 606/65 |
| 5,871,319 A | 2/1999 | Schneider | 411/107 |
| 6,197,065 B1 | 3/2001 | Martin et al. | 623/23.17 |
| 6,488,683 B2 * | 12/2002 | Lieberman | 606/263 |
| 6,508,841 B2 | 1/2003 | Martin et al. | 623/23.12 |
| 6,527,774 B2 | 3/2003 | Lieberman | 606/61 |
| 6,544,265 B2 | 4/2003 | Lieberman | 606/69 |
| 6,551,320 B2 | 4/2003 | Lieberman | 606/61 |
| 6,656,184 B1 * | 12/2003 | White et al. | 606/318 |
| 7,175,626 B2 | 2/2007 | Neff | 606/73 |
| 7,833,256 B2 * | 11/2010 | Biedermann et al. | 606/300 |
| 2005/0085815 A1 | 4/2005 | Harms et al. | 606/61 |
| 2005/0154390 A1 | 7/2005 | Biedermann et al. | 606/61 |
| 2006/0229615 A1 | 10/2006 | Abdou | 606/61 |
| 2007/0167948 A1 | 7/2007 | Abdou | 606/61 |
| 2008/0021465 A1 * | 1/2008 | Shadduck et al. | 606/61 |

FOREIGN PATENT DOCUMENTS

| | | |
|---|---|---|
| DE | 3538238 | 9/1986 |
| DE | 299 15 204 | 8/1999 |
| EP | 0172130 | 2/1986 |
| EP | 0374088 | 6/1990 |

(Continued)

*Primary Examiner* — Pedro Philogene
(74) *Attorney, Agent, or Firm* — Stroock & Stroock & Lavan LLP (57) ABSTRACT

A dynamic bone fixation element for securing an elongated fixation element such as, a longitudinal rod or bone plate, to a patient's bone, preferably a vertebra. The dynamic bone fixation element preferably includes a bone fixation element and a flexible element for connecting the bone fixation element to the elongated fixation element. The flexible element preferably permits the elongated fixation element to move with respect to the bone fixation element and hence with respect to the bone affixed thereto. The flexible element preferably permits extension and/or compression of the elongated fixation element with respect to the bone fixation element and polyaxially movement of the elongated fixation element with respect to the bone fixation element. The flexible element is preferably in the form of a spring or a spring-like flexible element.

19 Claims, 8 Drawing Sheets

FOREIGN PATENT DOCUMENTS

| | | |
|---|---|---|
| EP | 0820731 | 1/1998 |
| EP | 1273269 | 1/2003 |
| FR | 2634371 | 1/1990 |
| FR | 2697428 | 5/1994 |
| FR | 2784019 | 4/2000 |
| WO | WO 02/24087 | 3/2002 |

* cited by examiner

DYNAMIC STABILIZATION SYSTEM

CROSS REFERENCE TO RELATED APPLICATION

This application claims priority to U.S. provisional patent application Ser. No. 60/942,821, filed Jun. 8, 2007, the contents of which is hereby incorporated by reference in its entirety.

FIELD OF THE INVENTION

The present invention relates to a dynamic stabilization system for flexibly securing an elongated fixation element, such as a longitudinal rod or bone plate, to a patient's bone. The dynamic stabilization system preferably includes one or more dynamic bone fixation elements, which incorporate a bone fixation element, such as a bone screw, and a flexible element, such as a spring, for securing the elongated fixation element to the patient's bone so that the dynamic bone fixation element permits the elongated fixation element to move with respect to the bone fixation element and hence with respect to the bone affixed thereto.

BACKGROUND OF THE INVENTION

Millions of people suffer from back pain, frequently as a result of spinal compression or stenosis. Treatment of this condition is frequently accomplished by procedures such as spinal fusion which may involve the use of one or more intervertebral spacers and a rigid fixation system such as a bone plate or longitudinal rod in order to fuse, fix and/or stabilize the spine at one or more levels. In some patients, bone quality is often compromised and the resulting stresses from the use of a rigid fixation system may shear the bone. The use of a dynamic stabilization system may reduce the amount of associated stress and thus better protect the patient's bone.

One aspect of dynamic stabilization systems is to provide the greatest preservation of normal spinal motion and function while eliminating as much pain as possible.

SUMMARY OF THE INVENTION

A dynamic stabilization system for securing an elongated fixation element such as, a longitudinal rod or bone plate, to a patient's bone, preferably a vertebra, is disclosed. The dynamic stabilization system preferably includes one or more dynamic bone fixation elements. The dynamic bone fixation element preferably includes a bone fixation element, such as for example a bone screw, and a flexible element for connecting the bone fixation element to the elongated fixation element. The flexible element preferably permits the elongated fixation element to move with respect to the bone fixation element and hence with respect to the bone affixed thereto. The flexible element preferably permits extension and/or compression of the elongated fixation element with respect to the bone fixation element. The flexible element preferably also permits polyaxially movement of the elongated fixation element with respect to the bone fixation element. The flexible element is preferably in the form of a spring.

In one preferred embodiment, the dynamic bone fixation element includes a bone fixation element and a spring connected to the bone fixation element for securing the bone fixation element to the elongated fixation element so that the elongated fixation element is permitted to move with respect to the bone fixation element.

In another preferred embodiment, the dynamic bone fixation element includes an externally threaded bone screw for threadably engaging a patient's bone and a spring. The bone fixation element includes a proximal end, a distal end and an internal bore extending from the proximal end towards the distal end. The spring connects the bone fixation element to an elongated fixation element so that the elongated fixation element is permitted to polyaxially move with respect to the bone fixation element. The spring includes at least a portion that extends into the internal bore formed in the bone fixation element, the spring being connected to the internal bore adjacent to the distal end of the bone fixation element.

BRIEF DESCRIPTION OF THE DRAWINGS

The foregoing summary, as well as the following detailed description of the preferred embodiments of the application, will be better understood when read in conjunction with the appended drawings. For the purposes of illustrating the device of the present application, there is shown in the drawings preferred embodiments. It should be understood, however, that the application is not limited to the precise arrangements and instrumentalities shown, and certain features may be used singularly or in combination with other features. In the drawings.

DETAILED DESCRIPTION OF THE INVENTION

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments will now be described with reference to the drawings. In general, such embodiments relate to a dynamic stabilization system, by way of non-limiting example, a dynamic stabilization system for posterior spinal fixation. As will be described in greater detail below, the dynamic stabilization system may include one or more dynamic bone fixation elements for flexibly connecting an elongated fixation element to two or more bones. As will be described in greater detail below, the dynamic bone fixation element may include a bone fixation element and a flexible element for connecting the bone fixation element to the elongated fixation element. The flexible element preferably permits the elongated fixation element to move with respect to the bone fixation element and hence with respect to the bone affixed thereto.

While the dynamic stabilization system and the dynamic bone fixation element will be described as and may generally be used in the spine (for example, in the lumbar, thoracic or cervical regions), those skilled in the art will appreciate that the dynamic stabilization system and the dynamic bone fixation element may be used for dynamic fixation of other parts of the body such as, for example, joints, long bones or bones in the hand, face, feet, extremities, cranium, etc.

Figure 1:
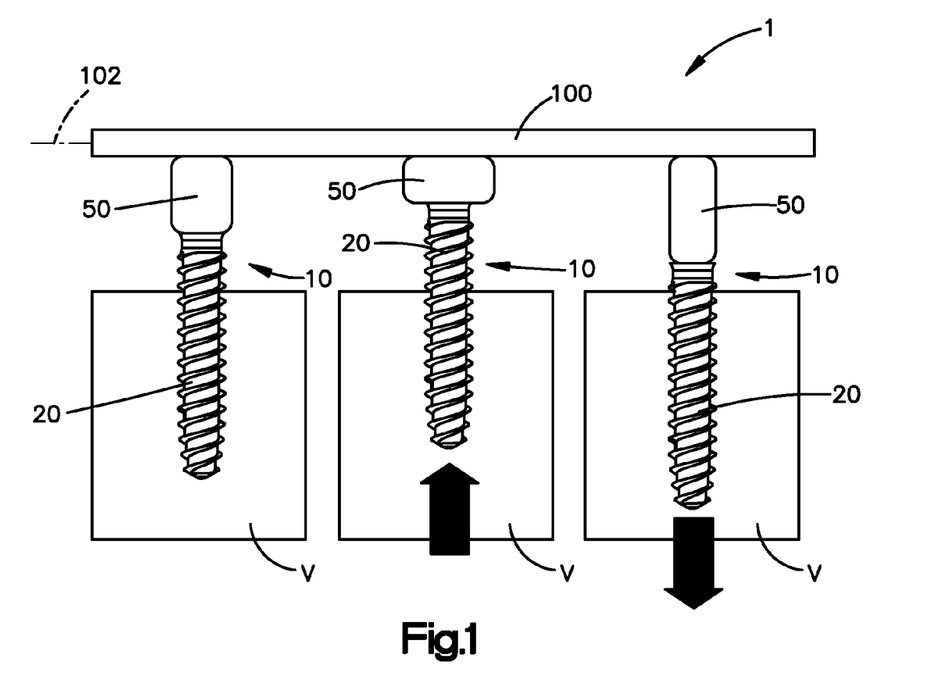
FIG. 1 illustrates a side-view of an exemplary embodiment of a dynamic stabilization system incorporating an exemplary embodiment of dynamic bone fixation elements coupled to an elongated fixation element.

As shown in FIG. 1, the dynamic stabilization system 1 preferably includes an elongated fixation element (shown here as an elongated rod) 100 and a plurality of dynamic bone fixation elements 10. The dynamic bone fixation elements 10 preferably include a bone fixation element (shown as bone screw) 20 and a flexible element (shown here as an elastomeric damper) 50 for securing the elongated fixation element 100 to a patient's bone, preferably a patient's vertebra V, so that the dynamic bone fixation element 10 permits the elongated fixation element 100 to move with respect to the bone affixed thereto.

As generally understood by one of ordinary skill in the art, the elongated fixation element 100 may be in the form of a longitudinal rod, bone plate, or any other device now or hereafter known in the art. It should be understood that the longitudinal rod may include, but is limited to, a solid rod, a non-solid rod, a flexible or dynamic rod, etc.

Also, as generally understood by one of ordinary skill in the art, the bone fixation element 20 may be, but is not limited to, a bone anchor, a hook, a spike, or other fastener, clamp or implant. Preferably, the bone fixation element 20 is a bone screw. It should be understood that the dynamic stabilization system 1 and the dynamic bone fixation element 10 are not limited in use to any particular type of bone fixation element 20 and/or elongated fixation element 100.

The flexible element 50 preferably permits extension and/or compression of the elongated fixation element 100 with respect to the bone fixation element 20. That is, the flexible element 50 preferably permits the elongated fixation element 100 to move vertically toward and away from the bone fixation element 20. The flexible element 50 also preferably permits the elongated fixation element 100 to polyaxially move with respect to the bone fixation element 20. That is, the flexible element 50 preferably permits the elongated fixation element 100 to move in any direction, for example, laterally (side to side), superior-inferior, both superior-inferior and laterally, etc. with respect to the bone fixation element 100, and hence with respect to the bone affixed thereto.

Figure 2:
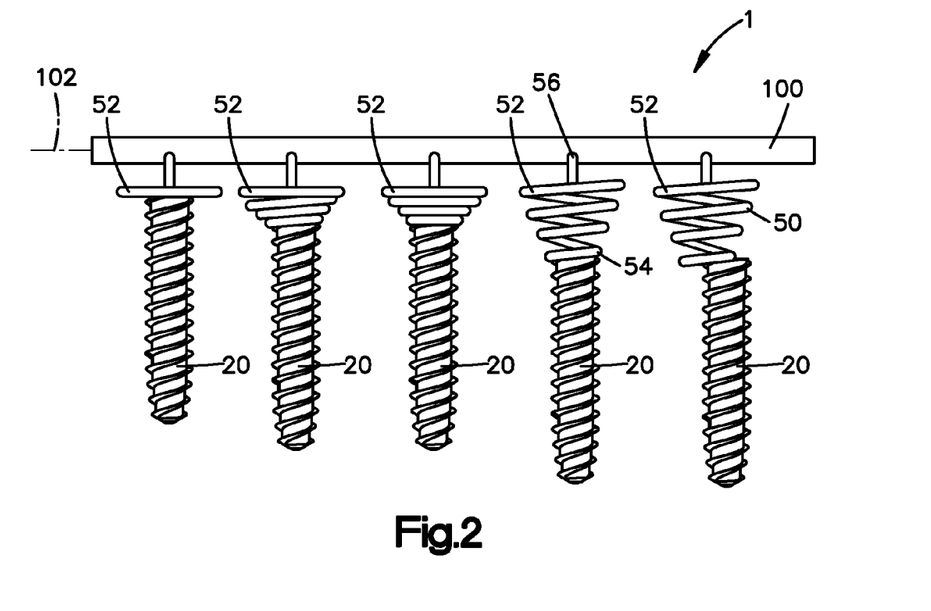
FIG. 2 illustrates a side-view of another exemplary embodiment of a dynamic stabilization system incorporating an exemplary embodiment of dynamic bone fixation elements coupled to an elongated fixation element.
Figure 2A:
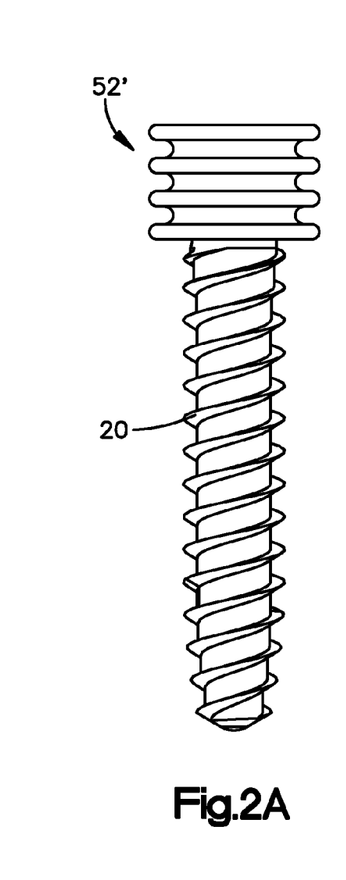
FIG. 2A illustrates a side-view of an exemplary embodiment of a dynamic bone fixation element.

The flexible element 50 may be any flexible element now or hereafter known including, but not limited to, an elastomer, a fluid filled bladder, etc. More preferably, as shown in FIG. 2, the flexible element 50 is in the form of a spring or a spring-like element 52 so that the elongated fixation element 100 is free to move in any direction with respect to the bone fixation element 20. The spring 52 may be in the form of a thin, flexible member, such as, for example, a thin-wire so that, as will be generally appreciated by one of ordinary skill in the art, the flexible member 50 acts as a spring having spring-like properties. Alternatively, as best shown in FIG. 2A, the flexible element 50 may be in the form of a spring-like bellows 52' formed from a metallic sheet such as, for example, titanium, stainless steel, etc. or rubber like material such as, for example, silicone, polyurethane, etc.

The spring-like flexible member 52 may be any spring now or hereafter known including, but not limited to, a helical spring, a compression spring, etc. The spring 52 may also have any pitch and/or shape now or hereafter known including, but not limited to, a constant pitch, a variable pitch, a conical shape, a barrel shape, an hourglass shape, etc. The spring 52 may include straight ends, hooked ends, offset ends, etc. As generally appreciated by one of ordinary skill in the art, modifying the pitch and/or shape of the spring enables the user to vary the spring constant (i.e., stiffness) of the spring 52 and hence of the dynamic bone fixation element 10 and dynamic stabilization system 1.

Referring to FIGS. 2 and 3A-3C, and as will be described in greater detail below, the spring 52 preferably includes a first portion 54 and a second portion 56 wherein the first portion 54 is preferably coupled to the bone fixation element 20 while the second portion 56 is preferably coupled to the elongated fixation element 100.

Figure 3A:
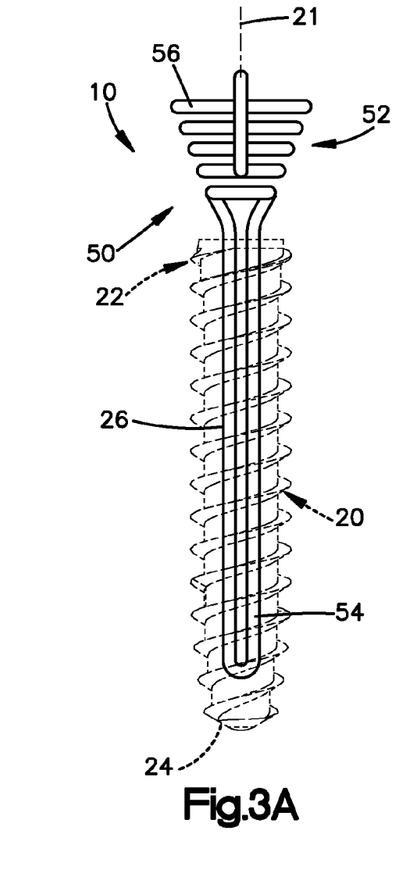
FIG. 3A illustrates a side-view of another exemplary embodiment of a dynamic bone fixation element.

As best shown in FIG. 3A, the bone fixation element 20 preferably includes a proximal end 22, a distal end 24 and an internal bore 26 extending from the proximal end 22 towards the distal end 24, the internal bore 26 being sized and configured to receive the first portion 54 of the spring 52 so that the first portion 54 of the spring 52 may be received by and/or embedded in the internal bore 26 of the bone fixation element 20. More preferably, the first portion 54 of the spring 52 extends into the internal bore 26 formed in the bone fixation element 20. As shown, the first portion 54 of the spring 52 may be in the form of a loop shaped member received within the internal bore 26 of the bone fixation element 20. The first portion 54 of the spring 52 is preferably connected to the internal bore 26 adjacent to the distal end 24 of the bone fixation element 20. As shown, the internal bore 26 is generally parallel to a longitudinal axis 21 of the bone fixation element 20. Alternatively, as will be generally appreciated by those skilled in the art, the internal bore 26 may take on other shapes including, but not limited to, a tapered bore.

Figure 3B:
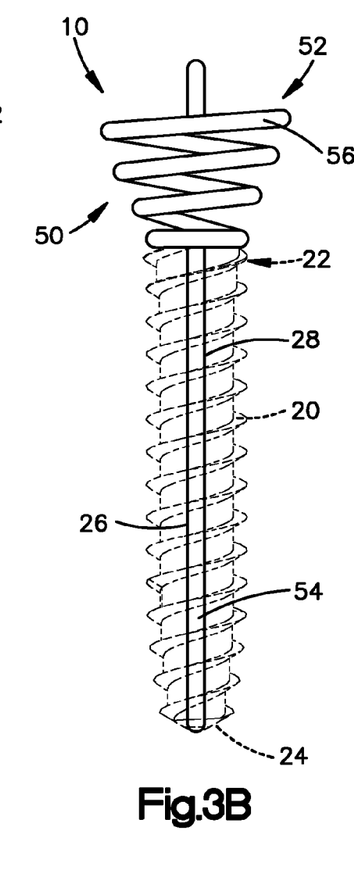
FIG. 3B illustrates a side-view of another exemplary embodiment of the dynamic bone fixation element.

Alternatively, as best shown in FIG. 3B, the internal bore 26 formed in the bone fixation element 20 may be in the form of a through bore 28 extending from the proximal end 22 to the distal end 24. The first portion 54 of the spring 52 being sized and configured to be received within the through bore 28 so that the first portion 54 of the spring 52 may extend from the proximal end 52 of the bone fixation element 20 to the distal end 24 of the bone fixation element 20.

Figure 3C:
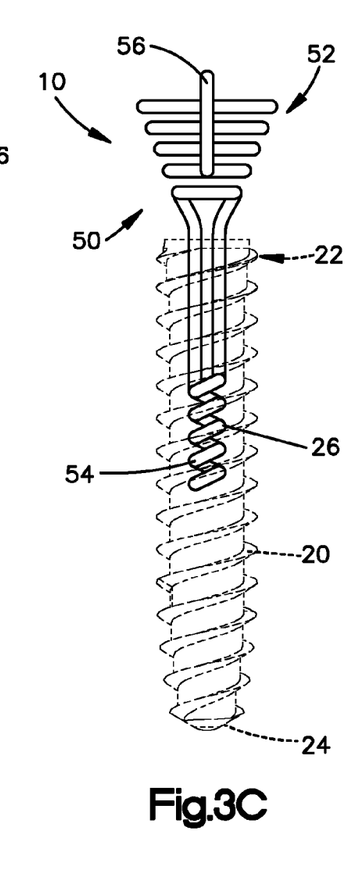
FIG. 3C illustrates a side-view of another exemplary embodiment of the dynamic bone fixation element.

Alternatively, as best shown in FIG. 3C, the first portion 54 of the spring 52 may be spirally wound and received within the internal bore 26 of the bone fixation element 20. Generally speaking, spirally winding the first portion 54 of the spring 52 permits increased flexibility of the spring 52.

Connection of the spring 52 to the bone fixation element 20 may be accomplished by any means now or hereafter known in the art including, but not limited to, mechanical means, welding, bonding, etc. For example, the spring 52 may be directly welded to the bone fixation element 20 as well as to the elongated fixation element 100. Alternatively and/or in addition, certain biocompatible adhesives that satisfy the strength and durability requirements of the particular application may be used instead of or in conjunction with welding. Such biocompatible adhesives may include, but are not limited to, cyanoacrylates, polyurethanes, epoxies, acrylics, etc.

Figure 4:
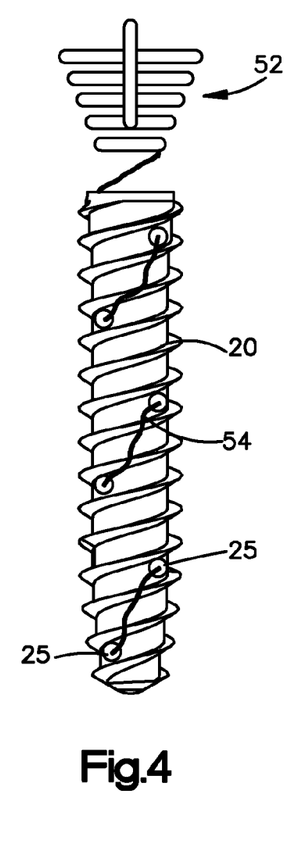
FIG. 4 illustrates a side-view of another exemplary embodiment of the dynamic bone fixation element.

Alternatively and/or in addition, mechanical means may be used for connecting the spring 52 to the bone fixation element 20 and/or the elongated fixation element 100. Mechanical means can be used instead of or in conjunction with welding and/or the use of adhesives. Mechanical means may include any number of means known in the art including, but not limited to, press-fit, friction-fit, screwing, tacking, etc. For example, the first portion 54 of the spring 52 may be mechanically fastened to the bone fixation element 20 by incorporating one or more fenestrations 25 in the bone fixation element 20 so that a portion of the spring 52 (preferably the first portion 54) may be passed therethrough to secure the spring 52 to the bone fixation element 20. As best shown in FIG. 4, a plurality of fenestrations 25 may be used so that the spring 52 (preferably the first portion 54) may be wrapped around and through the bone fixation element 20. As will be generally appreciated by those skilled in the art, any number of fenestrations 25 may be provided in the bone fixation element 20, such as, for example, one, two, three or more.

Figure 5:
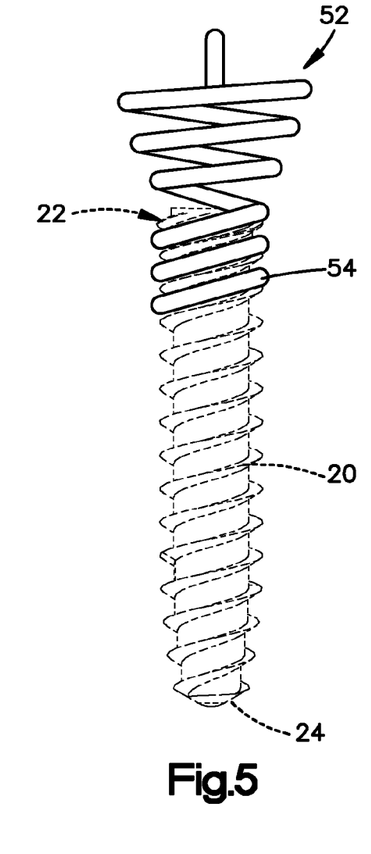
FIG. 5 illustrates a side-view of another exemplary embodiment of the dynamic bone fixation element.

Alternatively and/or in addition thereto, as best shown in FIG. 5, the first portion 54 of the spring 52 may be wound helically about the proximal end 22 of the bone fixation element 20. Preferably, the spring 52 may be wound helically about one or more threads formed on the bone screw.

Figure 6:
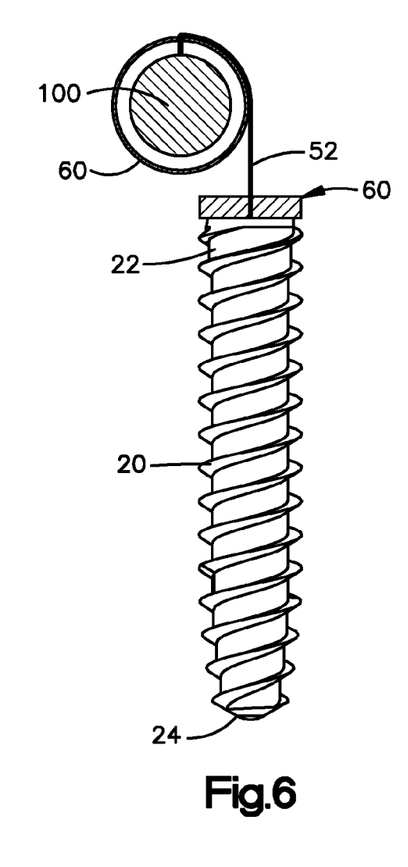
FIG. 6 illustrates a side-view of another exemplary embodiment of the dynamic bone fixation element.

Alternatively and/or in addition thereto, as best shown in FIG. 6, the spring 52 may be connected to the bone fixation element 20, preferably at the proximal end 22 of the bone fixation element 20, and/or to the elongated fixation element 100 via a housing 60 that surrounds at least a portion of the spring 52 and at least a portion of the bone fixation element 20, preferably at least a portion of the proximal end 22, and/or at least a portion of the elongated fixation element 100. The housing 60 may be, for example, a sleeve or a tube. The housing 60 may be sized and configured to include and/or encase the spring 52, and/or may be sized and configured to rotate around the central axis of the bone fixation element 20 and/or the elongated fixation element 100. Alternatively, the spring 52 may be coiled around the housing 60. In use, rotation of the housing 60 may cause the spring 52 to be preloaded to a desired tension or stiffness. Suitable materials for the housing 60 may include, but are not limited to, titanium, stainless steel or any of a variety of polymers.

Moreover, the bone fixation element 20 and spring 52 may be integrally formed. For example, the proximal end 22 of the bone fixation element 20 may be formed into a spring when machining.

As previously mentioned, the second portion 56 of the spring 52 is preferably located exterior of and preferably between the bone fixation element 20 and the elongated fixation element 100. As best shown in FIGS. 2 and 3A-3C, the second portion 56 of the spring 52 may be spirally wound in order to increase the overall flexibility provided by the spring 52. However, as will be generally appreciated by one of ordinary skill in the art, the second portion 56 of the spring 52 may take on any other form including, but not limited to, straight, non-wound, etc.

Connection of the spring 52 to the elongated fixation element 100 may be accomplished by any means now or hereafter known in the art including, but not limited to, mechanical means, welding, bonding, etc.

Figure 7:
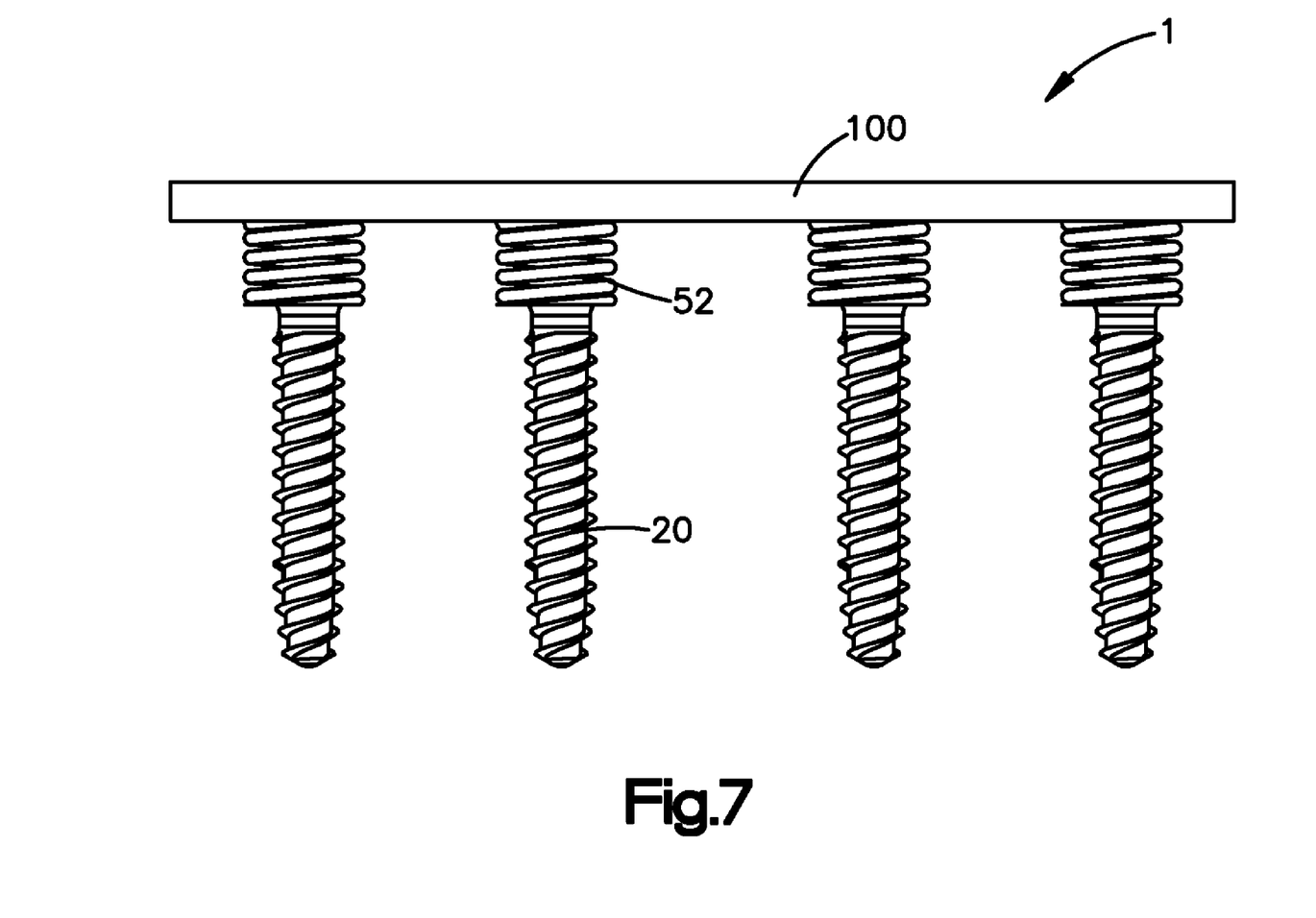
FIG. 7 illustrates a side-view of another exemplary embodiment of a dynamic stabilization system incorporating an exemplary embodiment of dynamic bone fixation elements coupled to an elongated fixation element.

In one preferred embodiment, as best shown in FIGS. 2 and 7, the spring 52 may be directly connected by, for example, welding to the elongated fixation element 100 and to the bone fixation element 20. One advantage of directly connecting the spring 52 to the elongated fixation element 100 and to the bone fixation element 20 is that the dynamic stabilization system 1, while still maintaining polyaxial positioning of the elongated fixation element 100 with respect to the bone fixation element 20, generally minimizes the overall height of the system. One way that this is achieved, for example, is by eliminating the need for the tulip-head body having a rod-receiving channel and locking cap, as is generally required by prior art polyaxial pedicle screws.

Alternatively, however, as will be readily appreciated by one or ordinary skill in the art, the spring 52 may be indirectly coupled to the elongated fixation element 100. For example, the dynamic bone fixation element 10 may incorporate a tulip-head body having a rod-receiving channel, the body being coupled to the bone fixation element 20 via a spring 52.

Figure 8A:
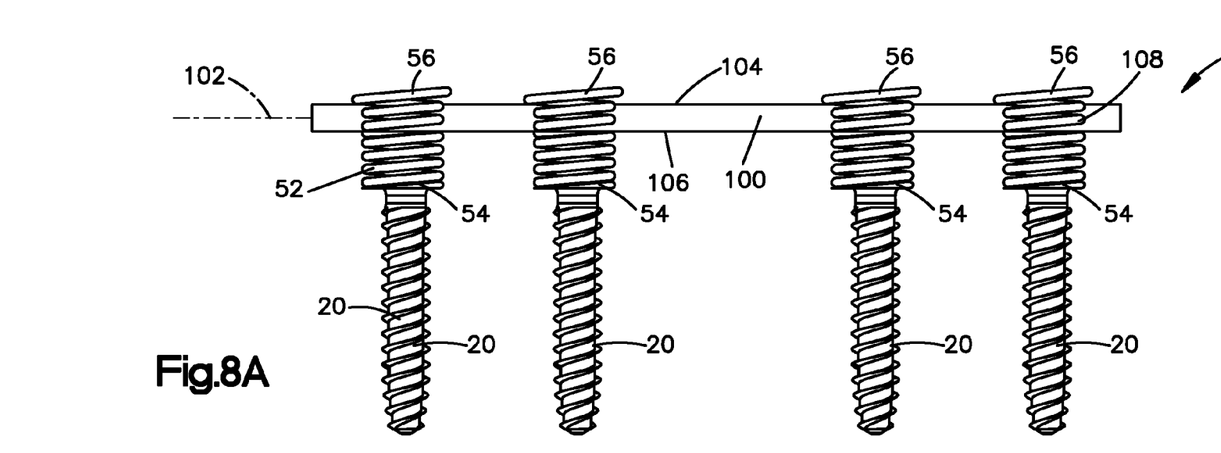
FIG. 8A illustrates a side-view of another exemplary embodiment of a dynamic stabilization system incorporating an exemplary embodiment of dynamic bone fixation elements coupled to an elongated fixation element.
Figure 8B:
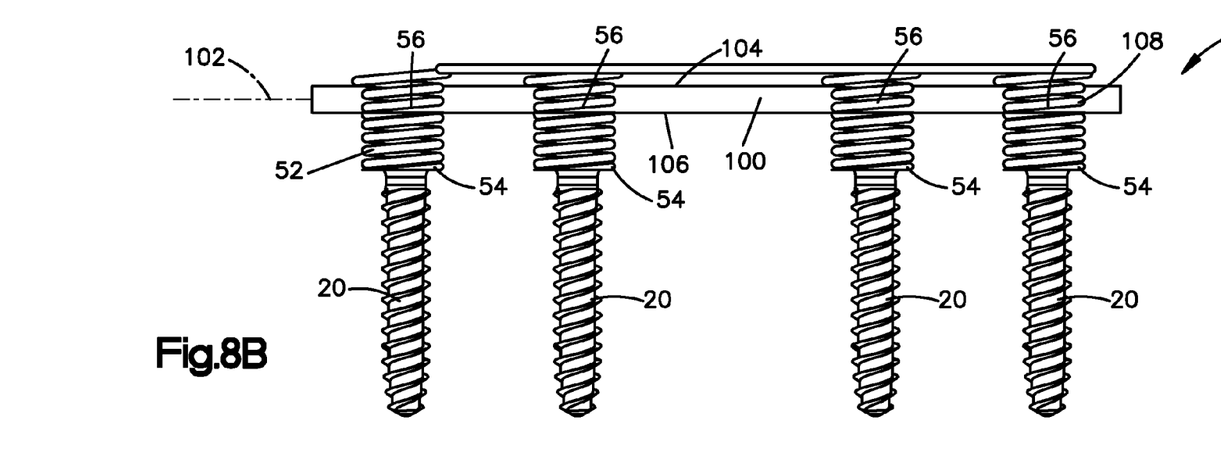
FIG. 8B illustrates a side-view of another exemplary embodiment of a dynamic stabilization system incorporating an exemplary embodiment of dynamic bone fixation elements coupled to an elongated fixation element.
Figure 9A:
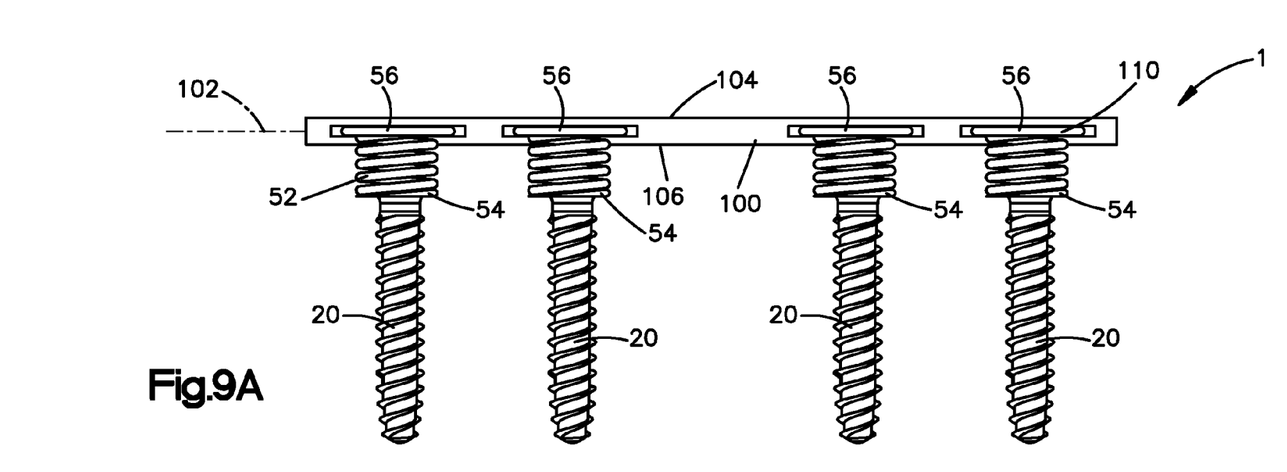
FIG. 9A illustrates a side-view of another exemplary embodiment of a dynamic stabilization system incorporating an exemplary embodiment of dynamic bone fixation elements coupled to an elongated fixation element.
Figure 9B:
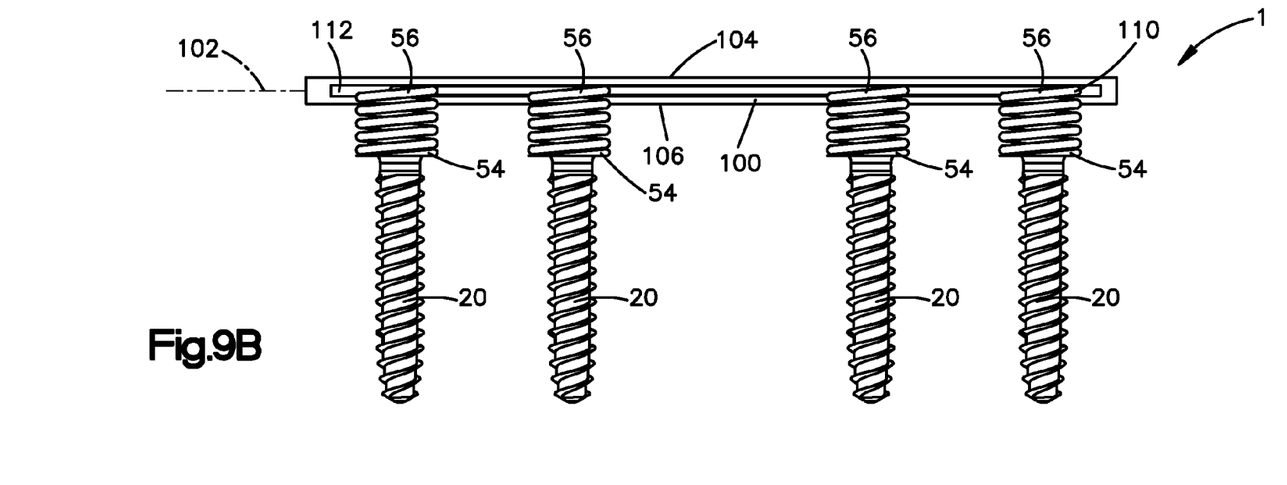
FIG. 9B illustrates a side-view of another exemplary embodiment of a dynamic stabilization system incorporating an exemplary embodiment of dynamic bone fixation elements coupled to an elongated fixation element.

Alternatively, the elongated fixation element 100 may include a plurality of full depth holes 108 (as best shown in FIGS. 8A and 8B) and/or partial holes 110 (as best shown in FIGS. 9A and 9B) extending from a bottom bone-facing surface 106 to a top surface 104 so that a portion, preferably the second portion 56, of the spring 52 can be inserted fully and/or partially into and/or through the full and/or partial depth holes 108, 110, respectively. Once inserted, the spring 52 can be welded, bonded and/or wound through the plurality of holes 108, 110. The plurality of full and/or partial depth holes 108, 110 may be formed perpendicular to or at oblique angles relative to a longitudinal axis 102 of the elongated fixation element 100.

In the case of full depth holes 108, preferably a portion of the spring 52 is completely inserted through the hole 108 and then partially and/or fully wound about the elongated fixation element 100. When partial depth holes 110 are used, the elongated fixation element 100 may also include an interior cannulated region 112 (as best shown in FIG. 9B) for receiving and/or housing at least a portion of the spring 52. The interior cannulated region 112 may be substantially parallel to or at an oblique angle with respect to the longitudinal axis 102 of the elongated fixation element 100. The spring 52 may be disposed at least partially (and/or fully) in the interior cannulated region 112 and may protrude through the plurality of partial holes 110 located on the bottom bone-facing surface 106 of the elongated fixation element 100, the holes 110 being in communication with the bone fixation elements 20 so that the spring 52 may be in communication with the dynamic bone fixation elements 10. As shown in FIGS. 8A, 8B, 9A and 9B, the springs 52 may or may not be connected to one another.

Figure 10:
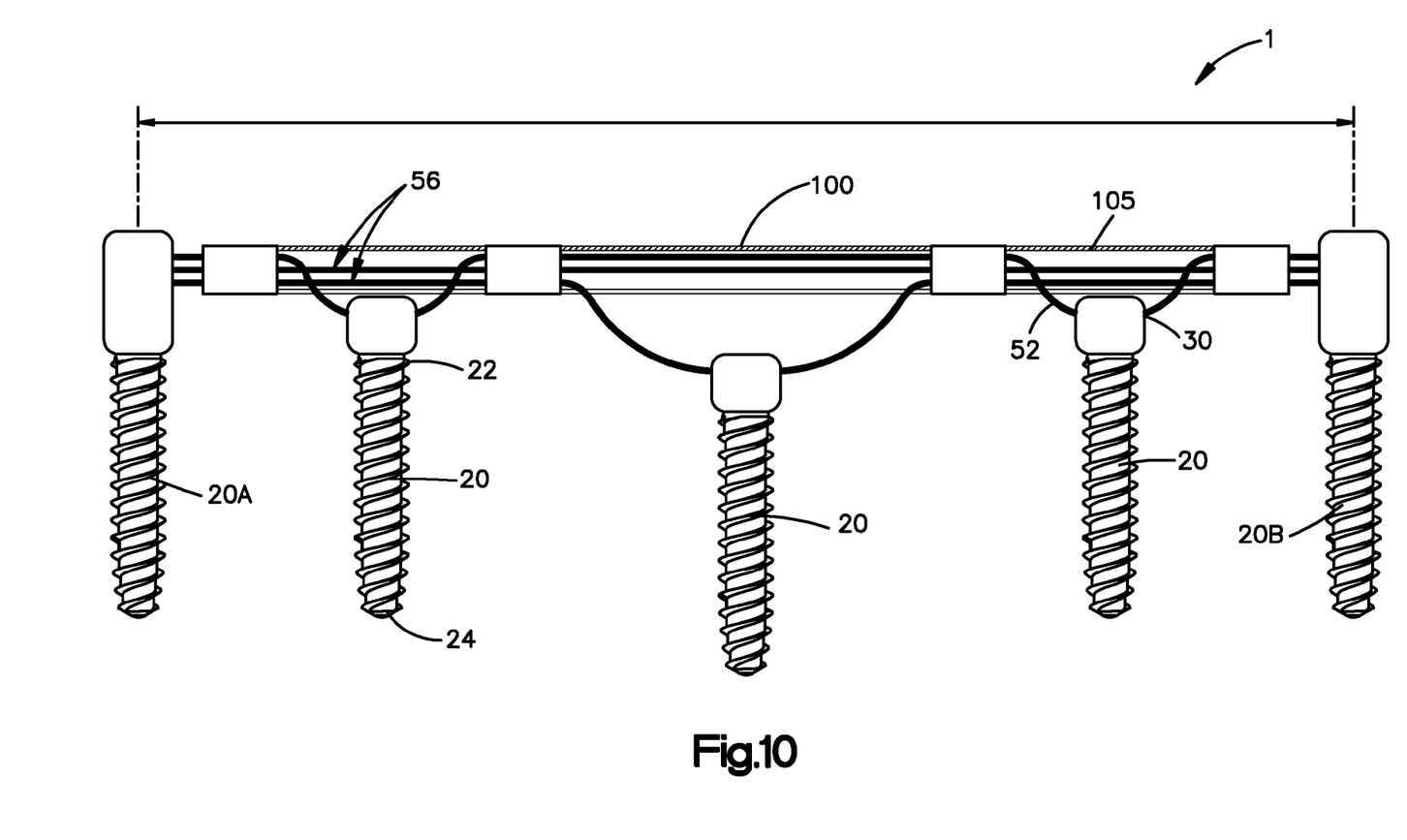
FIG. 10 illustrates a side-view of another exemplary embodiment of a dynamic stabilization system incorporating an exemplary embodiment of dynamic bone fixation elements coupled to an elongated fixation element.
Figure 11A:
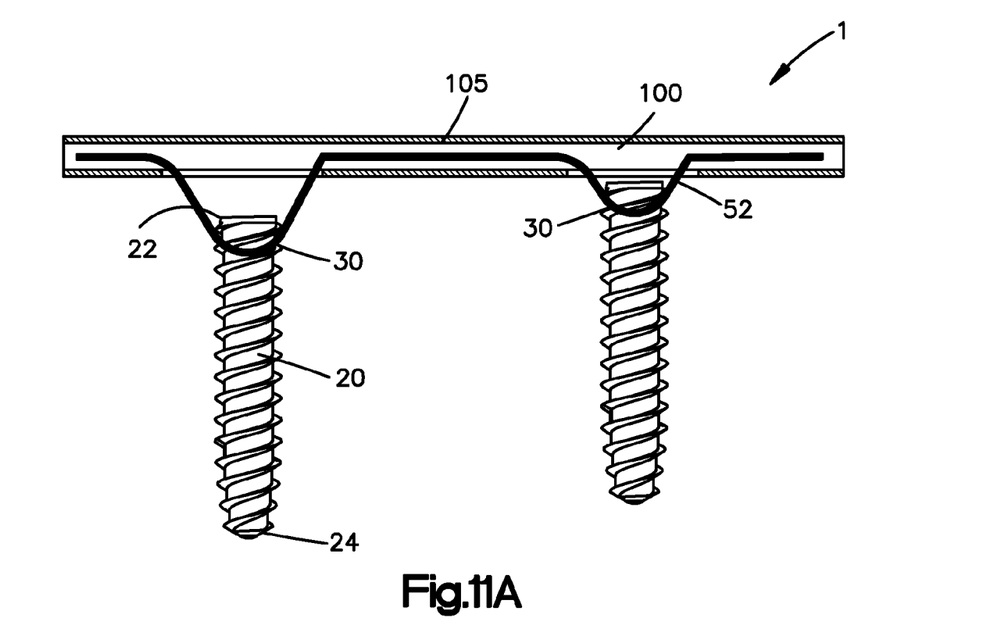
FIG. 11A illustrates a side-view of another exemplary embodiment of a dynamic stabilization system incorporating an exemplary embodiment of dynamic bone fixation elements coupled to an elongated fixation element.
Figure 11B:
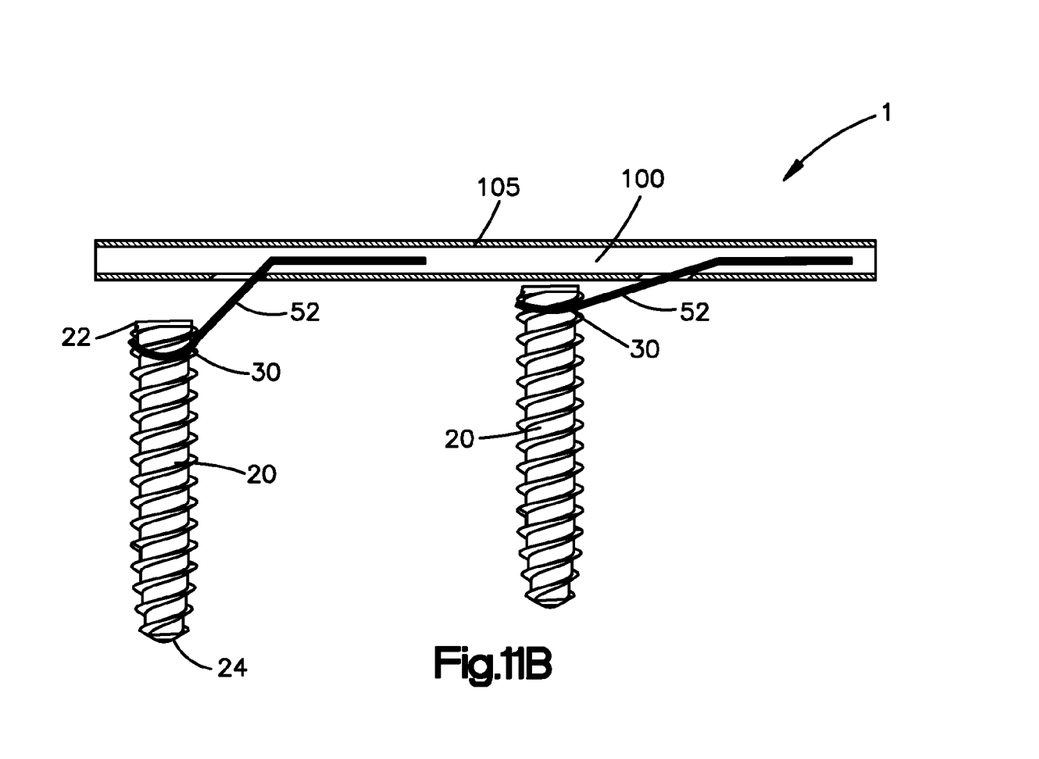
FIG. 11B illustrates a side-view of another exemplary embodiment of a dynamic stabilization system incorporating an exemplary embodiment of dynamic bone fixation elements coupled to an elongated fixation element.

Alternatively and/or in addition thereto, as best shown in FIGS. 10, 11A and 11B, the elongated fixation element 100 may include an internal passage or bore 105 for receiving at least a portion of the spring 52 therein. In use, as best shown in FIGS. 11A and 11B, the bone fixation elements 20 may be indirectly or flexibly coupled to the elongated fixation element 100 via one or more springs 52, which are at least partially disposed within the internal passage or bore 105 formed in the elongated fixation element 100. As shown in FIG. 11A, a single spring 52 passing in and/or through the internal passage or bore 105 and through multiple bone fixation elements 20 may be used. Alternatively, as best shown in FIG. 11B, multiple springs 52 may be used.

Alternatively, in use, some bone fixation elements 20 may be directly coupled to the elongated fixation element 100 and/or some bone fixation elements 20 may be indirectly or flexibly coupled to the elongated fixation element 100 via one or more springs 52. The indirectly coupled bone fixation elements 20 may include a bore hole 30 formed therein for receiving a portion of the spring 52 therein. Preferably, the bore hole 30 is disposed transversely through the proximal end 22 of the bone fixation element 20. As will be generally appreciated by those skilled in the art, the bore hole 30 may be formed however at an oblique angle with respect to the longitudinal axis of the bone fixation element 20 and/or may be formed in other parts of the bone fixation element 20 such as, for example, in an intermediate section between the proximal and distal ends 22, 24. By providing a construct that includes bone fixation elements 20 directly coupled to the elongated fixation element 100 as well as bone fixation elements 20 indirectly or flexibly coupled to the elongated fixation element 100, e.g., via a spring 52, between the directly coupled bone fixation elements 20, a user can ideally tailor directional forces to individual vertebrae.

For example, as best shown in FIG. 10, the internal passage or bore 105 formed in the elongated fixation element 100 may include one or more axially preloaded springs 56 that are disposed between a pair of bone fixation elements 20A, 20B. The axially preloaded springs 56 may be characterized by differing spring constants and/or other characteristics. The bone fixation elements 20 disposed between the bone fixation elements 20A, 20B are connected to the one or more axially preloaded springs 56. Axially preloaded springs 56 enable a range of flexibilities to be imparted to the bone fixation elements and provide dynamic stability to the system.

Connection between the bone fixation element 20 and the elongated fixation element 100 may be achieved by using one or more of a plurality of differing flexible elements 50 that may be supplied as part of a kit, wherein the flexible elements 50 may have varying spring constants (i.e., stiffness) so that the dynamic bone fixation system can be tailored to correct deformities of the spine, in which different forces are applied to different vertebrae to achieve a more ideal and beneficial dynamic fixation.

Where welding and/or bonding is incorporated, the surface area in contact with the flexible elements 50 is preferably maximized. For example, in one embodiment, the maximization of the surface area of contact may be achieved by forming a flat platform or a curved area on a portion of the flexible element 50, the curved portion having a concavity that matches the convexity of the elongated fixation element 100.

The dynamic bone fixation element 10 preferably is preassembled with the flexible element 50 preattached to the bone fixation element 20. The elongated fixation element 100 may be preassembled with the dynamic bone fixation element 10 attached thereto. Alternatively, the elongated fixation element 100 and dynamic bone fixation element 10 may be assembled preoperatively or intraoperatively.

The spring 52 can be formed out of any material that meets the flexibility and strength requirements for the application including, but not limited to, titanium, nitinol, nickel-titanium alloys, shape-memory materials, stainless steel alloys such as nivaflex, glass metals, or fiber-reinforced polymers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A dynamic stabilization system comprising:
   a bone fixation element including a proximal end, a distal end and an internal bore extending from the proximal end towards the distal end, the internal bore having an inner surface; and
   a spring connected to the bone fixation element for securing the bone fixation element to an elongated fixation element so that the elongated fixation element is permitted to move with respect to the bone fixation element;
   wherein the spring is received within the internal bore and in contact with and connected to the inner surface of the internal bore of the bone fixation element.

2. The dynamic stabilization system of claim 1, wherein the bone fixation element is a bone screw and the elongated fixation element is selected from one of a longitudinal rod and a bone plate.

3. The dynamic stabilization system of claim 1, wherein the spring permits extension and compression of the elongated fixation element with respect to the bone fixation element.

4. The dynamic stabilization system of claim 3, wherein the spring permits the elongated fixation element to polyaxially move with respect to the bone fixation element.

5. The dynamic stabilization system of claim 1, wherein the spring includes at least a portion that extends into the internal bore formed in the bone fixation element, the spring being connected to and contacting the inner surface of the internal bore adjacent to the distal end of the bone fixation element.

6. The dynamic stabilization system of claim 1, wherein the internal bore formed in the bone fixation element is a through bore extending from the proximal end to the distal end of the bone fixation element, the through bore being configured to receive at least a portion of the spring so that the spring extends from the proximal end to the distal end of the bone fixation element.

7. The dynamic stabilization system of claim 1, wherein the spring is connected to the bone fixation element and to the elongated fixation element by welding.

8. The dynamic stabilization system of claim 1, wherein the bone fixation element and the spring are integrally formed.

9. The dynamic stabilization system of claim 1, wherein the elongated fixation element includes one or more holes formed at least partially therein for receiving at least a portion of the spring.

10. The dynamic stabilization system of claim 1, wherein the spring is formed of metallic wire.

11. The dynamic stabilization system of claim 1, wherein the spring comprises a helical spring.

12. The dynamic stabilization system of claim 11, wherein the helical Spring is formed of wire.

13. A dynamic stabilization system comprising:
- an externally threaded bone screw for threadably engaging a patient's bone, the bone screw including a proximal end, a distal end and an internal bore extending from the proximal end towards the distal end; and
- a spring connected to the bone screw for securing the bone screw to an elongated fixation element so that the elongated fixation element is permitted to polyaxially move with respect to the bone screw;
- wherein the spring includes at least a portion that extends into the internal bore formed in the bone screw, the spring being directly connected to and in contact with the internal bore adjacent to the distal end of the bone screw.

14. The dynamic stabilization system of claim 13, wherein the spring permits extension and compression of the elongated fixation element with respect to the bone screw.

15. The dynamic stabilization system of claim 13, wherein the elongated fixation element is selected from one of a longitudinal rod and a bone plate.

16. The dynamic stabilization system of claim 13, wherein the spring is connected to the bone screw and to the elongated fixation element by welding. spring is formed of wire.

17. The dynamic stabilization system of claim 13, wherein the spring is formed of a metallic wire.

18. The dynamic stabilization system of claim 13, wherein the spring comprises a helical spring.

19. The dynamic stabilization system of claim 18, wherein the helical spring is formed of wire.

* * * * *